United States Patent [19]

Roseman et al.

[11] 4,402,693

[45] Sep. 6, 1983

[54] MEDICATED DEVICE HOLDER

[75] Inventors: Theodore J. Roseman; Glenford R. Derr, both of Portage, Mich.; Gilbert Schwartzman, Mamaroneck, N.Y.

[73] Assignee: The Upjohn Company, Kalamazoo, Mich.

[21] Appl. No.: 376,798

[22] Filed: May 10, 1982

Related U.S. Application Data

[63] Continuation-in-part of Ser. No. 261,337, May 7, 1981, abandoned.

[51] Int. Cl.³ ............................................. A61F 13/20
[52] U.S. Cl. .................................................. 604/890
[58] Field of Search ............... 604/890, 891, 892, 893, 604/894; 128/130–132; 424/19, 20, 21, 22, 23, 24

Primary Examiner—Richard J. Apley
Assistant Examiner—T. J. Wallen
Attorney, Agent, or Firm—Flynn, Thiel, Boutell & Tanis

[57] ABSTRACT

A medicated device comprises a substantially cylindrical, hollow body member having radially outwardly extending annular ridges at each end, a lengthwise slot, and inwardly extending flanges along the edges of the slot which have concave facing surfaces. A multi-layer, drug-bearing sheet material extends around the cylindrical member between and adjacent the annular ridges and has edge portions which extend into the slot. A cylindrical rod is disposed between the concave surfaces to clamp the sheet edge portions in the slot against the concave surfaces. End caps are mounted on each end of the cylindrical member, and each has a radially inwardly extending ridge which presses an adjacent edge of the sheet material against the cylindrical member.

12 Claims, 5 Drawing Figures

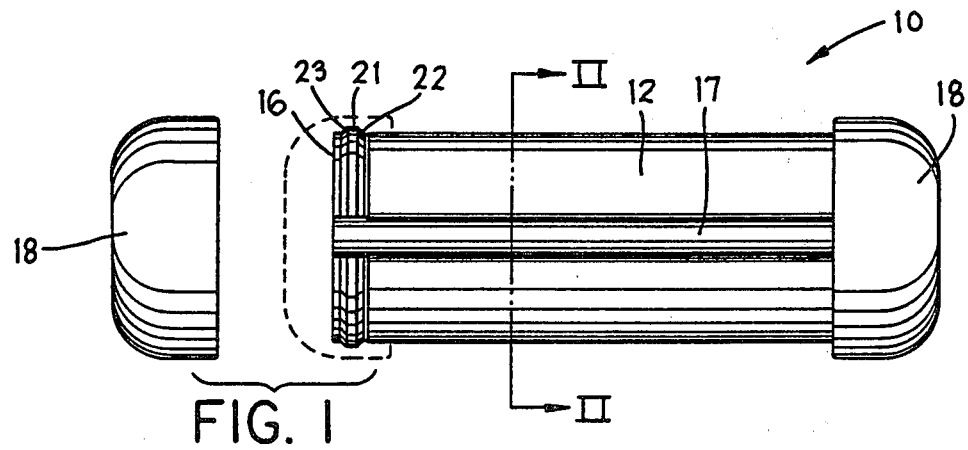
FIG. 1
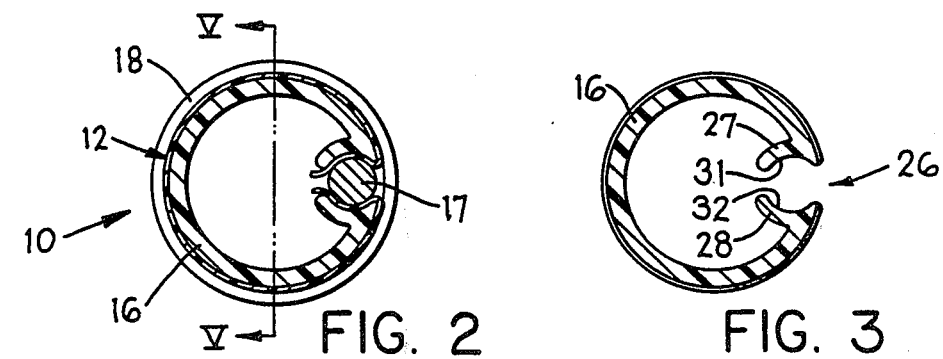
FIG. 2  FIG. 3
FIG. 4
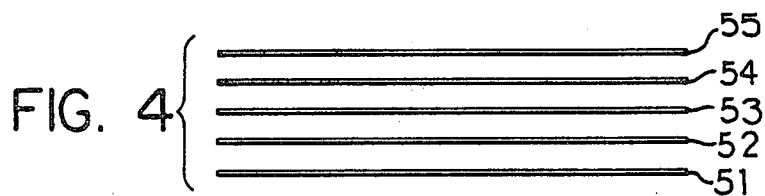
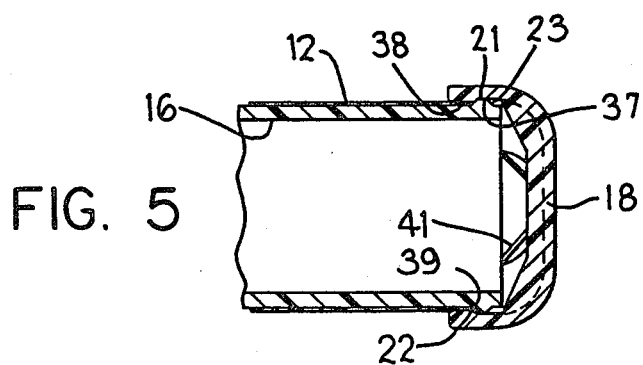
FIG. 5

MEDICATED DEVICE HOLDER

CROSS-REFERENCE TO RELATED APPLICATION

This application is a continuation-in-part of U.S. patent application Ser. No. 261,337, filed May 7, 1981, now abandoned.

FIELD OF THE INVENTION

This invention relates to a medicated device for rectally or vaginally administering a single, acute dose of a drug and, more particularly, to such a device in which the drug is administered at a rate which is essentially constant with time.

BACKGROUND OF THE INVENTION

Rectal or vaginal administration of therapeutic doses of numerous pharmacological agents has been accomplished with numerous medicated devices. U.S. Pat. No. 4,237,888, for example, discloses a medicated device for administering rectally or vaginally to a female mammal a lipophilic prostaglandin in order to effect a discrete event in the mammalian reproductive cycle. Such device comprises three primary components, namely, a tampon-type support, a first polymer film affixed to the support and containing the drug, and a second polymer film laminated onto the first film to control the rate of release of the drug from the first film. Although this device has been adequate for its intended purposes, it has not proved satisfactory in all respects. In particular, the rate-controlling, second film was applied by a dipping process which did not provide a uniform film for controlling the release rate of the drug. Thus, the drug was dispensed at an unpredictable rate. The drug-bearing, first film is capable of releasing the drug at rates up to ten times faster than the rate permitted by the rate-controlling, second film.

Accordingly, it is an object of the present invention to provide a medicated drug-delivery device for supporting a sheet comprising a drug-bearing film or membrane and a rate-controlling film or membrane in which a constant surface area of the rate-controlling film is exposed to vaginal or rectal fluid and no edge portions of the drug-bearing film are exposed to such fluid.

SUMMARY OF THE INVENTION

The objects of the invention, including those set forth above, are met by providing a substantially cylindrical, hollow, relatively rigid, but resiliently flexible, body member having radially outwardly extending annular ridges adjacent its opposite axial ends and having a lengthwise slot with radially inwardly extending flanges adjacent the edges of the slot, the facing surfaces of such flanges being concave. A multi-layer sheet material, which sheet material has a drug-bearing film and a drug release rate-controlling film, extends circumferentially around the cylindrical body member between and adjacent the annular ridges and has opposite longitudinal edge portions which extend into the slot. A cylindrical rod having a length substantially the same as that of the cylindrical body member and having a diameter approximately equal to the centerline distance between the concave surfaces of the radially inwardly extending flanges of the cylindrical body member is snugly and releasably received between the concave surfaces to hold the edge portions of the sheet material firmly against the concave surfaces. The cylindrical body member is preferably impermeable to the drug. Alternatively, the multi-layer sheet material can include a non-permeable support film attached to the drug-bearing film on the side thereof remote from the rate-controlling film.

Similar end caps are mounted upon the opposite axial ends of the cylindrical body member, each end cap having a cylindrical recess therein of slightly greater inside diameter than the outside diameter of the annular ridges on the cylindrical body member, and having a radially inwardly extending annular ridge of slightly lesser inside diameter than the outside diameter of the annular ridges on the cylindrical body member. The annular ridge on each end cap is received around the cylindrical body member axially inwardly of the adjacent annular ridge on the cylindrical body member and holds the adjacent axial edge of the sheet material firmly against the surface of the cylindrical body member.

BRIEF DESCRIPTION OF THE DRAWINGS

Other objects, purposes and advantages of this invention will be apparent to persons skilled in the art upon reading the following specification and inspecting the accompanying drawings, in which:

FIG. 1 is an exploded, elevational view of a drug-delivery device embodying the present invention;

FIG. 2 is a sectional view taken along the line II—II of FIG. 1; p FIG. 3 is a sectional view of a cylindrical member which is a component of the device of FIG. 2;

FIG. 4 is an exploded view of the layers of film and adhesive of a multi-layer sheet material utilized in the present invention; and FIG. 5 is a sectional view taken along the line V—V of FIG. 2.

Certain terminology will be used in the following description for convenience in reference only and will not be limiting. The words "in" and "out" will respectively refer to directions toward and away from the geometric center of the device and designated parts thereof. Such terminology will include the words specifically mentioned, derivatives thereof and words of similar import.

DETAILED DESCRIPTION

FIGS. 1 and 2 illustrate a medicated device holder 10 adapted to hold a drug-bearing sheet 12. The holder 10 comprises a substantially cylindrical body member 16, a cylindrical rod 17 and a pair of end caps 18. The body member 16, the rod 17 and the end caps 18 are made of biocompatible, moldable, polymeric materials which are safe and effective for use in the human body and which are impermeable to the drug contained in the sheet 12. In the presently preferred embodiment, the body member 16, the rod 17 and the end caps 18 are made from polypropylene, for example, polypropylene sold under the designation USS F120F, a product of Novamont, Inc. of Pittsburgh, Pa., a subsidiary of United States Steel Corporation. The body member 16, the rod 17 and the end caps 18 do not permit substantial diffusion therethrough of the drug contained in the sheet 12.

The cylindrical body member 16 is hollow and relatively rigid, but resiliently flexible. A radially outwardly extending annular ridge 21 is provided at each end thereof and defines as inclined, axially inwardly facing annular shoulder 22. The axially outer portion of the annular ridge 21 has a bevel 23 for a purpose set forth hereinafter.

As best shown in FIG. 3, a lengthwise slot 26 is provided in one side of the cylindrical body member 16. Inwardly extending flanges 27 and 28 are provided along the edges of the slot 26, extend the full length of the member 16 and are preferably formed integrally with the member 16. The respective facing surfaces 31 and 32 of the flanges 27 and 28 are preferably concave and spaced from each other.

The cylindrical rod 17 is substantially the same length as the cylindrical body member 16 and has a diameter approximately equal to or slightly greater than the centerline distance between the concave surfaces 31 and 32 of the flanges 27 and 28 of the cylindrical body member 16.

As shown in FIG. 5, each of the end caps 18 has a substantially cylindrical recess 37 therein which is of slightly greater inside diameter than the outside diameter of the annular ridges 21 on the cylindrical body member 16. A radially inwardly extending annular ridge 38 is provided at the axially inner end of the recess 37 of each end cap 18 and said ridge has an inside diameter which is slightly greater than the outside diameter of the cylindrical body member 16, but is slightly less than the outside diameter of the annular ridges 21 on the cylindrical body member 16. An inclined, axially facing annular shoulder 39 is provided on the annular ridge 38 and is adapted to seat against the shoulder 22. If desired, as shown in FIG. 5, reinforcing ribs 41 may be provided in each end cap 18 to give the end cap rigidity.

The sheet 12 preferably has three polymer films 51, 53 and 55 with adhesive layers 52 and 54 therebetween. In the preferred embodiment, and as illustrated in FIG. 4, the thicknesses of the three polymer films 51, 53 and 55 typically range from 1 to 5 mils each. The thicknesses of the adhesive layers are preferably less than 0.2 mils each.

Film 51 is a support layer which gives strength and durability to the multi-layer sheet 12 and said film 51 preferably is impermeable with respect to the drug carried by the sheet 12. The support film 51 preferably is made of polyethylene homopolymer, for example, polyethylene having a density of 0.922 g/cc (ASTM D-1505) and a melt index of 2.0 g/10 min. (ASTM D-1238). When total impermeability of the support film 51 by the drug is less critical, for example, when the cylindrical member 16 is made from a material impermeable by the drug, the support film 51 can be made from an ethylene-vinyl acetate copolymer, for example, UE 637, which contains 9% vinyl acetate and which is a product of U.S.I. Chemicals.

The film 53 is a drug-bearing layer which has a drug, such as a prostaglandin, dissolved and suspended therethrough. The film 53 is preferably made from either an ethylene-vinyl acetate copolymer or a urethane polymer and is not rate-limiting as to the release of the drug therefrom. In the preferred embodiment, the film 53 is made from an ether polyurethane, for example, Estane 5714-F1, a product of the Chemical Division of B. F. Goodrich Company. In the preferred embodiment, the drug is a lipophilic anti-luteal/oxytocic prostaglandin as described in U.S. Pat. No. 4,237,888, the entire contents of which are incorporated herein by reference.

The film 55 is a rate-controlling layer which limits the rate at which the drug from the drug-bearing film 53 is released to the rectal or vaginal tissues. In the preferred embodiment, the film 55 is an ethylene-vinyl acetate copolymer containing 28 wt. % vinyl acetate, for example, UE 645, a product of U.S.I. Chemicals. An ethylene-vinyl acetate copolymer containing 18 wt. % vinyl acetate, for example UE 630, a product of U.S.I. Chemicals, also is satisfactory.

The layers 52 and 54 are adhesion layers which bond the support film 51, drug-bearing film 53 and rate controlling film 55 together. The adhesive layers 52 and 54 are preferably an ethylene-vinyl acetate copolymer, for example, UE 645 mentioned above.

As shown in FIGS. 2 and 5, a substantially rectangular piece of the multi-layer sheet 12 is wrapped around the cylindrical body member 16 with the rate-controlling layer 55 being disposed outermost. Each of two axial edges of the sheet 12 is disposed adjacent a respective one of the ridges 21 on the cylindrical body member 16, and the two circumferential edges thereof extend into the slot 26 past the concave surfaces 31 and 32 on the flanges 27 and 28 of the cylindrical body member 16. The cylindrical rod 17 is then placed parallel to the slot 26 and is pushed inwardly into the slot 26 until, as shown in FIG. 2, it is centered between the concave surfaces 31 and 32 and clamps the circumferential edge portions of the sheet 12 within the slot 26 firmly against the concave surfaces 31 and 32, whereby such edge portions are protected from exposure to rectal or vaginal fluids. The cylindrical body member 16 is relatively rigid, but resiliently flexible, so that the flanges 27 and 28 can move apart slightly as the rod 17 is inserted therebetween and will then resiliently urge the edge portions of the sheet 12 firmly against the rod 17.

An end cap 18 is then pressed onto each end of the cylindrical body member 16 until the inwardly extending annular ridge 38 is located axially inwardly of and has snapped down over the outwardly extending annular ridge 21 on the cylindrical body member 16, so that the annular shoulders 22 and 39 respectively provided on the cylindrical body member 16 and the end cap 18 are disposed against each other, as shown in FIG. 5. This prevents inadvertent removal or dislodging of the end cap 18 from the cylindrical body member 16. In this position, as best shown in FIG. 5, the annular ridge 38 on the end cap 18 firmly presses the axial edges of the multi-layer sheet 12 firmly against the cylindrical body member 16, whereby such edges are protected from exposure to vaginal or rectal fluids. Each end cap 18 must be properly centered and coaxially aligned with the axis of the cylindrical body member 16 as it is pressed onto the cylindrical body member 16 to avoid wrinkling the sheet 12. The bevels 23 facilitate the requisite alignment between the end caps 18 and the cylindrical body member 16, and reduce the forces required to snap the end caps 18 into place.

The assembled device thus has all edges of the drug-bearing film 53 protected from exposure to rectal or vaginal fluids, so as to preclude a direct release of the drug from the drug-bearing film 53 to the rectal or vaginal fluid at an uncontrolled rate. In addition, a predetermined and constant surface area of the rate-controlling film 55 is exposed to the rectal or vaginal fluid, thereby providing the desired dosage at a substantially constant rate.

So long as the support film 51 of the sheet 12 is impermeable to the drug carried by the drug-bearing layer 53, thereby inhibiting diffusion of the drug into the holder 10, it is not essential that the cylindrical body member 16 be made of a material impermeable by the drug. If, however, the cylindrical body member 16 is made from a material impermeable to the drug, the support film 51 and adhesion layer 52 can be omitted from the sheet 12. The sheet 12 is then slightly more difficult to handle and extra care is required to mount it on the holder 10, but the cost of fabricating the sheet 12 is reduced.

The materials used to make the cylindrical body member 16, the cylindrical rod 17, the end caps 18 and the drug-bearing sheet 12 are physiologically inert, resilient, water-insoluble and safe for use in the human body. Further details concerning the criteria for a medicated device of this type are set forth in U.S. Pat. No. 4,237,888 and need not be repeated herein.

Although a particular preferred embodiment of the invention has been disclosed in detail for illustrative purposes, it will be recognized that variations or modifications of the disclosed apparatus, including the rearrangement of parts, lie within the scope of the present invention. For example, minor variations in the geometry of the holder are within the scope of the invention, so long as the shape of the holder is consistent with the dimensions of the vaginal or rectal vault, a constant surface area of the rate-controlling membrane is exposed, and no portions of the drug-bearing film are exposed to the rectal or vaginal fluids.

The embodiments of the invention in which an exclusive property or privilege is claimed are defined as follows:

1. A medicated device adapted for rate-controlled vaginal or rectal administration of a therapeutic drug comprising:
   an elongated body member;
   a piece of sheet material extending around said body member and having adjacent first edge portions extending lengthwise of said body member and second edge portions close to the opposite axial ends of said body member, said sheet material being comprised of a drug-bearing film and a rate control film adhered to the outer surface of said drug-bearing film;
   clamp means for securing said first edge portions of said sheet material with respect to the body member and for protecting said first edge portions from exposure externally of said device; and
   cap means engageable with the ends of said body member for securing said second edge portions of said sheet material with respect to said body member and for protecting said second edge portions from exposure externally of said device.

2. The medicated device of claim 1, wherein said elongated body member is substantially cylindrical and relatively rigid but resiliently flexible.

3. The medicated device of claim 2, wherein said body member is hollow and said clamp means includes:
   means defining a lengthwise slot in said body member and spaced, facing surfaces within said slot on opposite sides thereof, said first edge portions of said sheet material extending into said slot; and
   elongated rod means having a width approximately equal to the distance between said facing surfaces and receivable therebetween for firmly holding each said first edge portion of said sheet material against a respective said facing surface.

4. The medicated device of claim 3, wherein each said facing surface is substantially concave and wherein said rod means is a substantially cylindrical rod having a length substantially equal to the length of said body member.

5. The medicated device of claim 4, wherein said body member has a radially inwardly extending flange along each edge of said lengthwise slot therein, each said concave surface being provided on a respective said flange.

6. The medicated device of claim 2, wherein:
   said body member has a radially outwardly extending annular ridge adjacent each end thereof, said second edge portions of said sheet material each being located adjacent a said annular ridge on said body member; and
   said cap means includes a pair of similar end caps adapted to be mounted on respective ends of said body member, each said end cap having a substantially cylindrical recess therein of larger diameter than said body member and having a radially inwardly extending annular ridge on the surface of said recess of slightly lesser inside diameter than the outside diameter of said annular ridges on said body member, said annular ridge on said end cap being located axially inwardly of said annular ridge on said body member and holding a respective said second edge portion of said sheet material firmly against said body member when said end cap is mounted on said body member.

7. The medicated device of claim 6, wherein the axially outer portion of each said annular ridge on said body member is beveled.

8. The medicated device of claim 1, wherein said sheet material includes a support film adhered to the inner surface of said drug-bearing film.

9. The medicated device of claim 8, wherein said support film of said sheet material is impermeable with respect to said drug in said drug-bearing film of said sheet material.

10. A medicated device adapted for rate-controlled vaginal or rectal administration to a female mammal of a therapeutic drug, comprising:
   a cylindrical and relatively rigid but resiliently flexible body member having a lengthwise slot therein, having facing concave surfaces provided in said slot on opposite sides thereof, and having radially outwardly extending annular ridges adjacent its opposite axial ends;
   a sheet material extending around said body member between said annular ridges thereon and having first edge portions adjacent said annular ridges and adjacent second edge portions extending into said slot, said sheet material including a drug-bearing film, a rate-controlling film, a support film substantially impervious to said drug, and adhesive means for securing said drug-bearing film to the inner surface of said rate-controlling film and the outer surface of said support film;
   rod means having a diameter approximately equal to the centerline distance between said concave surfaces and receivable therebetween for holding each said second edge portion firmly against a respective said concave surface; and
   a pair of similar end caps mounted upon respective ends of said body member, each said end cap having a radially inwardly extending annular ridge of slightly lesser inside diameter than the outside diameter of said ridges on said body member and arranged to be received around said member inwardly of said annular ridge on said body member for engagement with said first edge portions of said sheet material;

whereby all edges of said sheet material are protected from exposure externally of the device.

11. The medicated device of claim 10, wherein said body member is hollow and has a radially inwardly extending flange adjacent each edge of said slot therein, said concave surfaces each being provided on a respective said flange.

12. A medicated device adapted for rate-controlled vaginal or rectal administration of a therapeutic drug comprising:

an elongated body member;

a piece of sheet material extending around said body member and having adjacent first edge portions extending lengthwise of said body member and second edge portions close to the opposite axial ends of said body member, said sheet material including a drug-bearing film, a rate-control film and adhesive means for securing said rate-control film to the outer surface of said drug-bearing film, one of said body member and the inner side of said sheet material being impervious to said drug;

clamp means for securing said first edge portions of said sheet material with respect to the body member and for protecting said first edge portions from exposure externally of said device; and cap means engageable with the ends of said body member for securing said second edge portions of said sheet material with respect to said body member and for protecting said second edge portions from exposure externally of said device.

* * * * *